United States Patent
Tezuka

(10) Patent No.: US 11,974,871 B2
(45) Date of Patent: May 7, 2024

(54) RADIATION IMAGING SYSTEM INCLUDING A RADIATION IMAGING APPARATUS, A RELAY APPARATUS, AND A SYSTEM CONTROL APPARATUS, METHOD OF CONTROLLING RADIATION IMAGING APPARATUS, AND COMPUTER READABLE STORAGE MEDIUM THEREFOR

(71) Applicant: CANON KABUSHIKI KAISHA, Tokyo (JP)

(72) Inventor: Shimpei Tezuka, Tochigi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 151 days.

(21) Appl. No.: 17/528,071

(22) Filed: Nov. 16, 2021

(65) Prior Publication Data

US 2022/0167939 A1 Jun. 2, 2022

(30) Foreign Application Priority Data

Nov. 27, 2020 (JP) .................................. 2020-196897

(51) Int. Cl.
*A61B 6/00* (2006.01)
*A61B 6/40* (2024.01)
(Continued)

(52) U.S. Cl.
CPC .............. *A61B 6/487* (2013.01); *A61B 6/405* (2013.01); *A61B 6/4233* (2013.01); *A61B 6/461* (2013.01);
(Continued)

(58) Field of Classification Search
CPC .. A61B 6/40; A61B 6/405; A61B 6/42; A61B 6/4208; A61B 6/4233;
(Continued)

(56) References Cited

U.S. PATENT DOCUMENTS 5,448,614 A * 9/1995 Suzuki ..................... H05G 1/60
378/115
5,917,882 A * 6/1999 Khutoryansky ......... H05G 1/58
378/98.2
(Continued)

FOREIGN PATENT DOCUMENTS

CN 102396217 A 3/2012
CN 110623682 A 12/2019
(Continued)

*Primary Examiner* — Allen C. Ho
(74) *Attorney, Agent, or Firm* — CANON U.S.A., INC. IP Division

(57) ABSTRACT

An imaging control unit in a radiation imaging apparatus causes imaging in a plurality of modes varying in a setting value, and causes standby driving to reduce signals stored in a plurality of pixels during a period in which the plurality of pixels is not irradiated with radiation. The plurality of modes includes a first mode for first imaging using a first setting value and a second mode for second imaging using a second setting value different from the first setting value after the first imaging. The imaging control unit causes the standby driving using a setting value closer to the second setting value than to the first setting value in response to end of the first imaging in causing the second imaging.

11 Claims, 9 Drawing Sheets

(51) Int. Cl.
    *A61B 6/42* (2024.01)
    *A61B 6/46* (2024.01)
    *G01N 23/04* (2018.01)

(52) U.S. Cl.
    CPC .............. *A61B 6/465* (2013.01); *A61B 6/467* (2013.01); *A61B 6/488* (2013.01); *A61B 6/5258* (2013.01); *A61B 6/54* (2013.01); *A61B 6/542* (2013.01); *A61B 6/545* (2013.01); *A61B 6/563* (2013.01); *A61B 6/566* (2013.01); *G01N 23/043* (2013.01); *G01N 2223/306* (2013.01)

(58) Field of Classification Search
    CPC ......... A61B 6/4283; A61B 6/46; A61B 6/461; A61B 6/462; A61B 6/463; A61B 6/465; A61B 6/467; A61B 6/486; A61B 6/487; A61B 6/488; A61B 6/5258; A61B 6/54; A61B 6/542; A61B 6/545; A61B 6/56; A61B 6/563; A61B 6/566
    USPC ....................... 378/42, 62, 114–116
See application file for complete search history.

(56) References Cited

U.S. PATENT DOCUMENTS

| | | | | |
|---|---|---|---|---|
| 8,358,740 | B2 * | 1/2013 | Nakatsugawa | A61B 6/586 378/116 |
| 8,363,786 | B2 * | 1/2013 | Nakatsugawa | A61B 6/4441 378/42 |
| 8,829,438 | B2 * | 9/2014 | Sato | H04N 25/60 250/336.1 |
| 9,020,097 | B2 * | 4/2015 | Iwakiri | A61B 6/4283 378/42 |
| 10,159,455 | B2 * | 12/2018 | Takanaka | H05G 1/30 |
| 10,162,067 | B2 * | 12/2018 | Mako | G01T 1/247 |
| 10,751,022 | B2 * | 8/2020 | Ishii | A61B 6/4233 |
| 10,768,122 | B2 * | 9/2020 | Tamura | G01N 23/04 |
| 10,918,353 | B2 * | 2/2021 | Tezuka | G01T 1/175 |
| 11,079,341 | B2 * | 8/2021 | Tezuka | A61B 6/486 |
| 11,157,059 | B2 * | 10/2021 | Yokoyama | H04N 5/32 |
| 11,357,457 | B2 * | 6/2022 | Aida | A61B 6/544 |
| 11,382,590 | B2 * | 7/2022 | Niwa | A61B 6/542 |
| 2011/0309262 | A1 | 12/2011 | Sato | |

FOREIGN PATENT DOCUMENTS

| | | |
|---|---|---|
| CN | 111374687 A | 7/2020 |
| JP | 2018014682 A | 1/2018 |
| JP | 2018019147 A | 2/2018 |

* cited by examiner

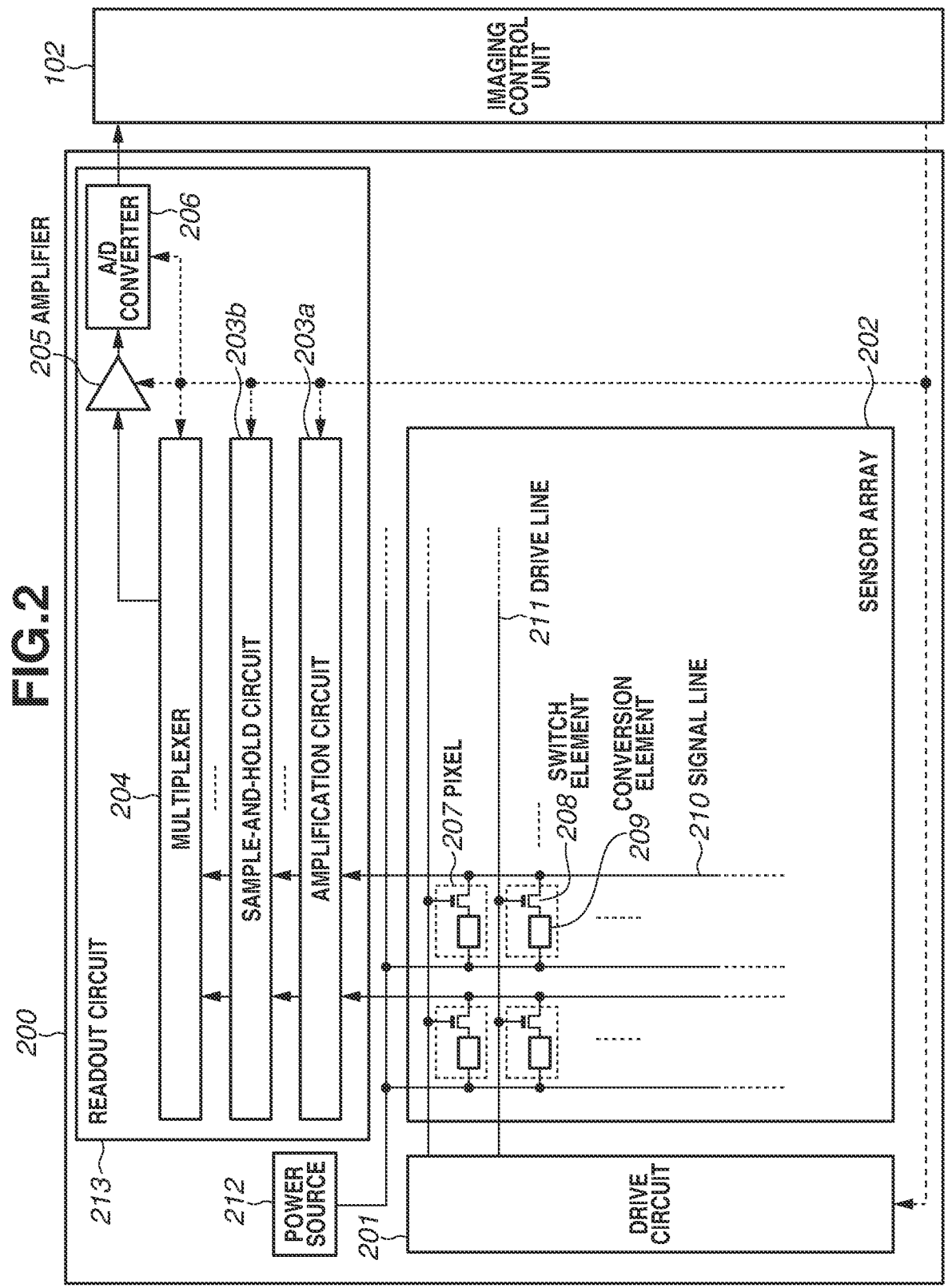

FIG.3A

| TARGET SWITCH | IMAGING MODE SETTING | IMAGING PARAMETERS |
|---|---|---|
| FLUOROSCOPY SWITCH (FOR CONTINUOUS FLUOROSCOPY) | A | 30 fps/2 × 2/12 inch/GAIN SETTING 1 |
| FLUOROSCOPY SWITCH (FOR PULSE FLUOROSCOPY) | B | 15 fps/2 × 2/17 inch/GAIN SETTING 2 |
| IMAGING SWITCH | C | 4 fps/1 × 1/17 inch/GAIN SETTING 3 |

FIG.3B

| TARGET SWITCH | IMAGING MODE SETTING | IMAGING PARAMETERS |
|---|---|---|
| FLUOROSCOPY SWITCH (FOR CONTINUOUS FLUOROSCOPY) | INVALID (NOT TO BE USED) | NO SETTING |
| FLUOROSCOPY SWITCH (FOR PULSE FLUOROSCOPY) | INVALID (NOT TO BE USED) | NO SETTING |
| IMAGING SWITCH | D | SINGLE/1 × 1/17 inch/GAIN SETTING 3 |

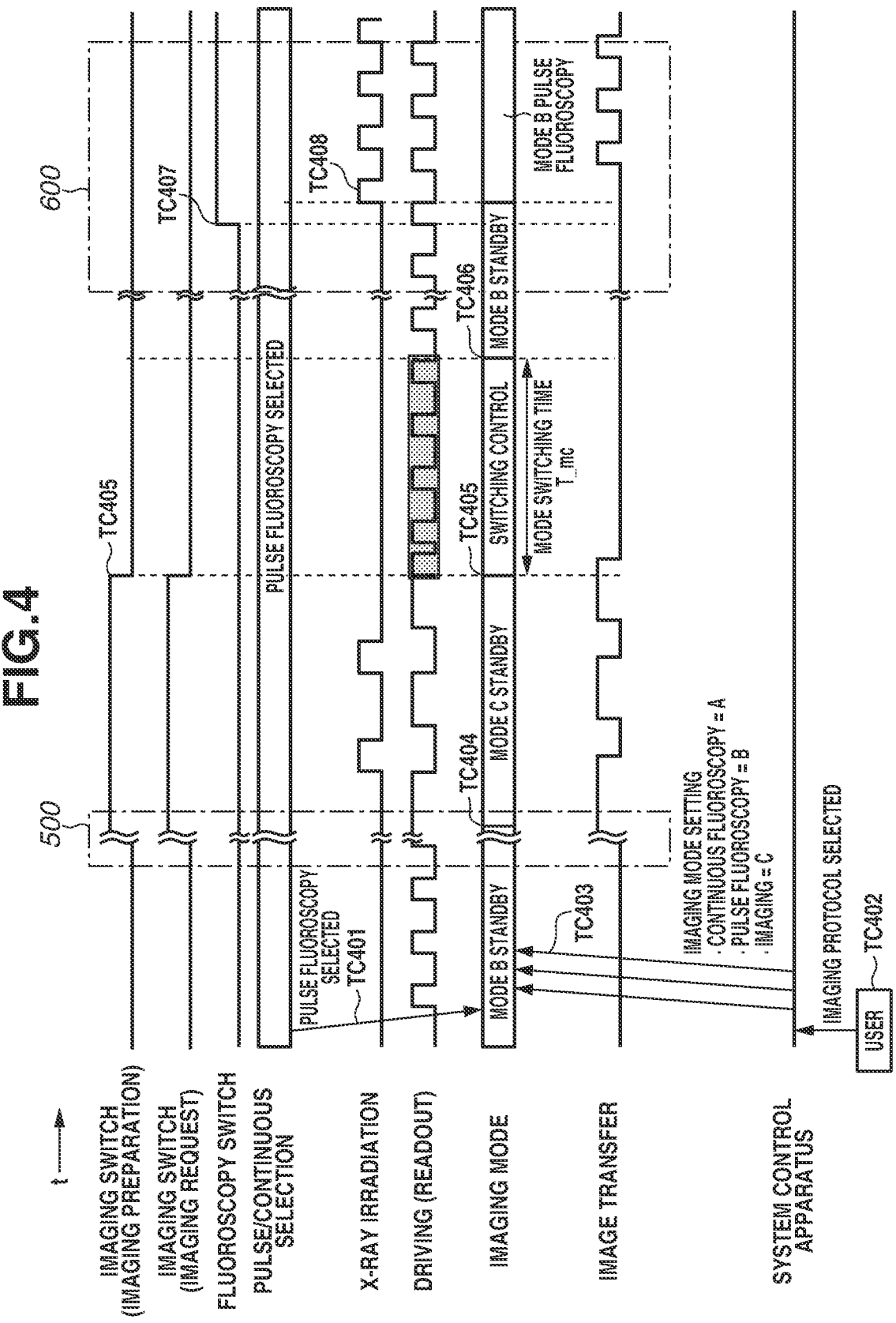

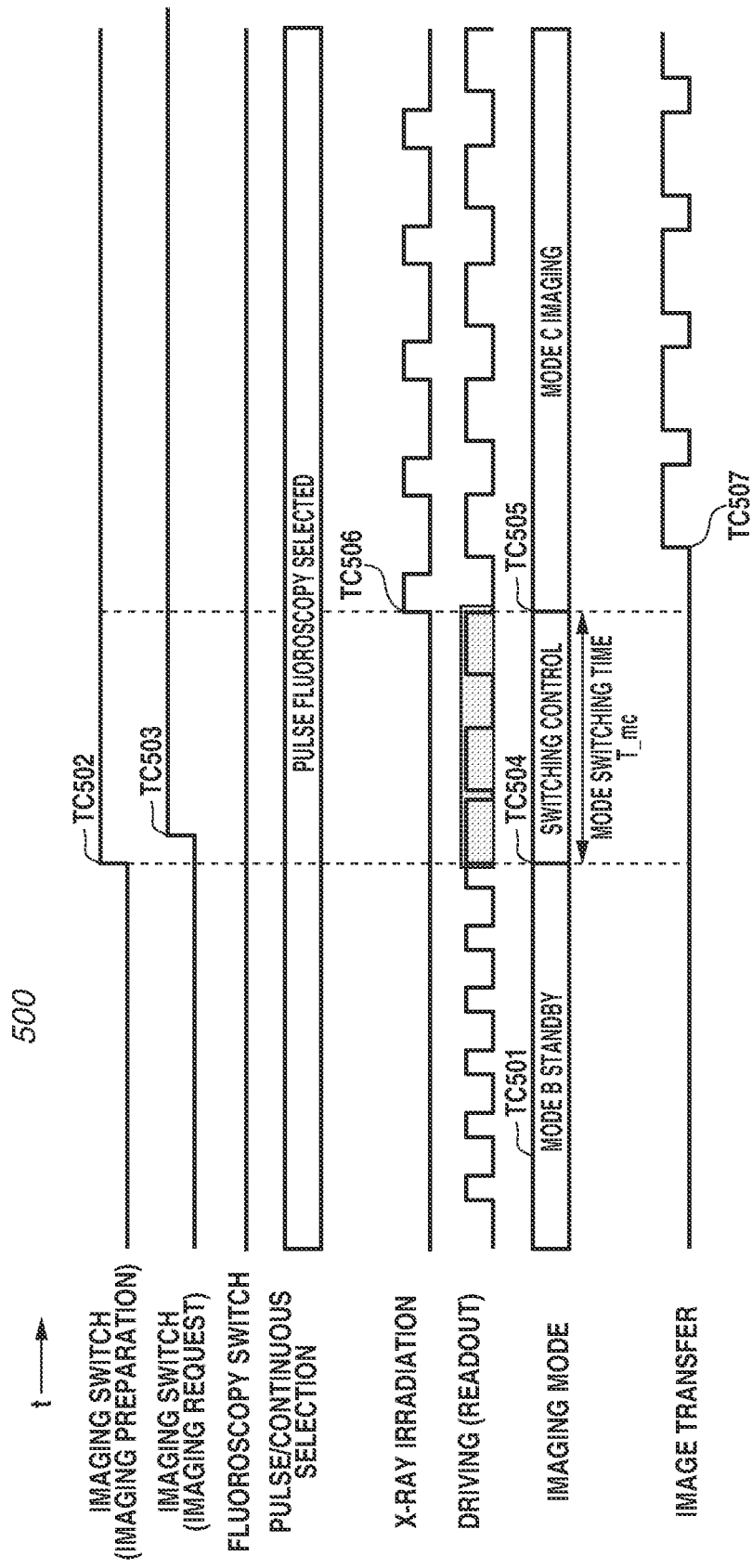

RADIATION IMAGING SYSTEM INCLUDING A RADIATION IMAGING APPARATUS, A RELAY APPARATUS, AND A SYSTEM CONTROL APPARATUS, METHOD OF CONTROLLING RADIATION IMAGING APPARATUS, AND COMPUTER READABLE STORAGE MEDIUM THEREFOR

BACKGROUND

Technical Field

One disclosed aspect of the embodiments relates to a radiation imaging apparatus, a radiation imaging system, a method of controlling a radiation imaging apparatus, and a computer readable storage medium therefor for acquiring an intensity distribution of radiation passing through an object, in an image.

Description of the Related Art

There is known a radiation imaging apparatus used in medical image diagnosis or other purposes with radiation such as X-rays that includes a sensor array, a two-dimensional array of pixels each with a combination of a switch such as a thin-film transistor (TFT) and a conversion element such as a photoelectric conversion element. Image data acquired in the radiation imaging apparatus is transferred to a control apparatus of the radiation imaging apparatus or an external apparatus such as an image processing apparatus, via a communications unit used in optical fiber communication using optical modules, wired communication such as Ethernet®, or wireless communication. For example, in medical image diagnosis, such a radiation imaging apparatus is used in acquiring digital radiation images through still-image capturing such as general imaging, or moving-image capturing such as fluoroscopic or continuous imaging.

Such a radiation imaging apparatus operates in a plurality of imaging modes suitable for purposes and usages of imaging, and switches those modes for various purposes. For example, a radiation imaging apparatus called a fluoroscopic apparatus can operate in two different imaging modes: a first imaging mode used to perform imaging operation called fluoroscopy to observe movements of an imaging target, and a second imaging mode to perform imaging operation called imaging to record an imaging target in diagnosis. The first imaging mode uses a fluoroscopy switch in performing fluoroscopy imaging operation, and the second imaging mode uses an imaging switch in performing recording imaging operation. For example, the first imaging mode provides high framerates and gain with low radiation doses in performing fluoroscopy imaging operation. The second imaging mode provides low framerates and gain with high radiation doses in performing diagnosis or recording imaging operation to carry out moving-image capturing with low speed or still-image capturing to capture individual images.

Such a radiation imaging apparatus repeats standby driving to reduce the dark current component likely to accumulate in pixels until the next capturing is started, during a standby period up to the next imaging, as discussed in Japanese Patent Application Laid-Open No. 2018-019147. Meanwhile, as discussed in Japanese Patent Application Laid-Open No. 2018-014682 a radiation imaging apparatus to perform imaging in a plurality of imaging modes can suffer an artifact that occurs in an image acquired in an imaging mode switched from another mode. To counteract the issue, the radiation imaging apparatus performs switching control to reduce the artifact in a changed imaging mode. The switching control is performable with the sensor array driven the same way as that before the change.

An embodiment of the disclosure takes into account switching control performed during a standby period in a radiation imaging apparatus to perform imaging in a plurality of imaging modes.

An embodiment of the disclosure is directed to a radiation imaging apparatus to perform imaging in a plurality of imaging modes that can perform control switching to an imaging mode suitable for use on a fluoroscopic apparatus during a standby period.

According to an aspect of the disclosure, a radiation imaging apparatus includes a radiation imaging unit configured to perform imaging of a radiation image in one frame by performing driving of a plurality of pixels to use signals stored in the plurality of pixels based on radiation irradiating the plurality of pixels arranged in a matrix, and an imaging control unit configured to control the imaging by controlling the driving based on a setting value. The imaging control unit causes the radiation imaging unit to perform the imaging in a plurality of modes varying in the setting value. The imaging control unit causes the radiation imaging unit to perform standby driving of driving the plurality of pixels to reduce signals stored in the plurality of pixels during a period in which the plurality of pixels is not irradiated with radiation. The plurality of modes includes a first mode in which the radiation imaging unit performs first imaging using a first setting value and a second mode in which the radiation imaging unit performs second imaging using a second setting value different from the first setting value after the first imaging. The imaging control unit causes the radiation imaging unit to perform the standby driving using the setting value closer to the second setting value than to the first setting value in response to end of the first imaging in causing the radiation imaging unit to perform the second imaging.

Further features of the disclosure will become apparent from the following description of exemplary embodiments with reference to the attached drawings.

BRIEF DESCRIPTION OF THE DRAWINGS

FIG. 2 is a diagram illustrating an internal configuration example of a radiation imaging unit.

FIGS. 3A and 3B are diagrams each illustrating a setting example of a setting unit of the radiation imaging apparatus.

FIG. 4 is a timing chart illustrating an imaging operation example of the radiation imaging system according to the first exemplary embodiment.

FIG. 5 is a timing chart illustrating an imaging operation example of the radiation imaging system according to the first exemplary embodiment.

DESCRIPTION OF THE EMBODIMENTS

Some exemplary embodiments of the disclosure will be described below with reference to the attached drawings. The term "radiation" includes alpha rays, beta rays, gamma rays, particle rays, and cosmic rays, in addition to X-rays. Further, the following exemplary embodiments can be combined as appropriate, and a mode with a combination of exemplary embodiments as appropriate is also included as an exemplary embodiment of the disclosure.

In the exemplary embodiments of the disclosure, a radiation imaging apparatus offers a solution to an issue related to switching control in a standby period. For example, standby driven the same way as that in the imaging operation immediately before the standby period is unlikely to cause an artifact in an image in the next imaging that is performed through no change, allowing an image to be acquired in a short period after a press of the imaging switch. However, imaging modes are often switched in realty. For example, the radiation imaging apparatus used as a fluoroscopic apparatus uses a fluoroscopy imaging mode to observe an imaging target and switches to a recording imaging mode to perform still-image capturing. In other words, it should be taken into consideration what type of sensor-array driving control to be performed up to the next imaging in a different imaging mode from the preceding one during in a standby period, and the disclosure provides novel standby driving in a radiation imaging apparatus to perform imaging in a plurality of imaging modes.

Figure 1:
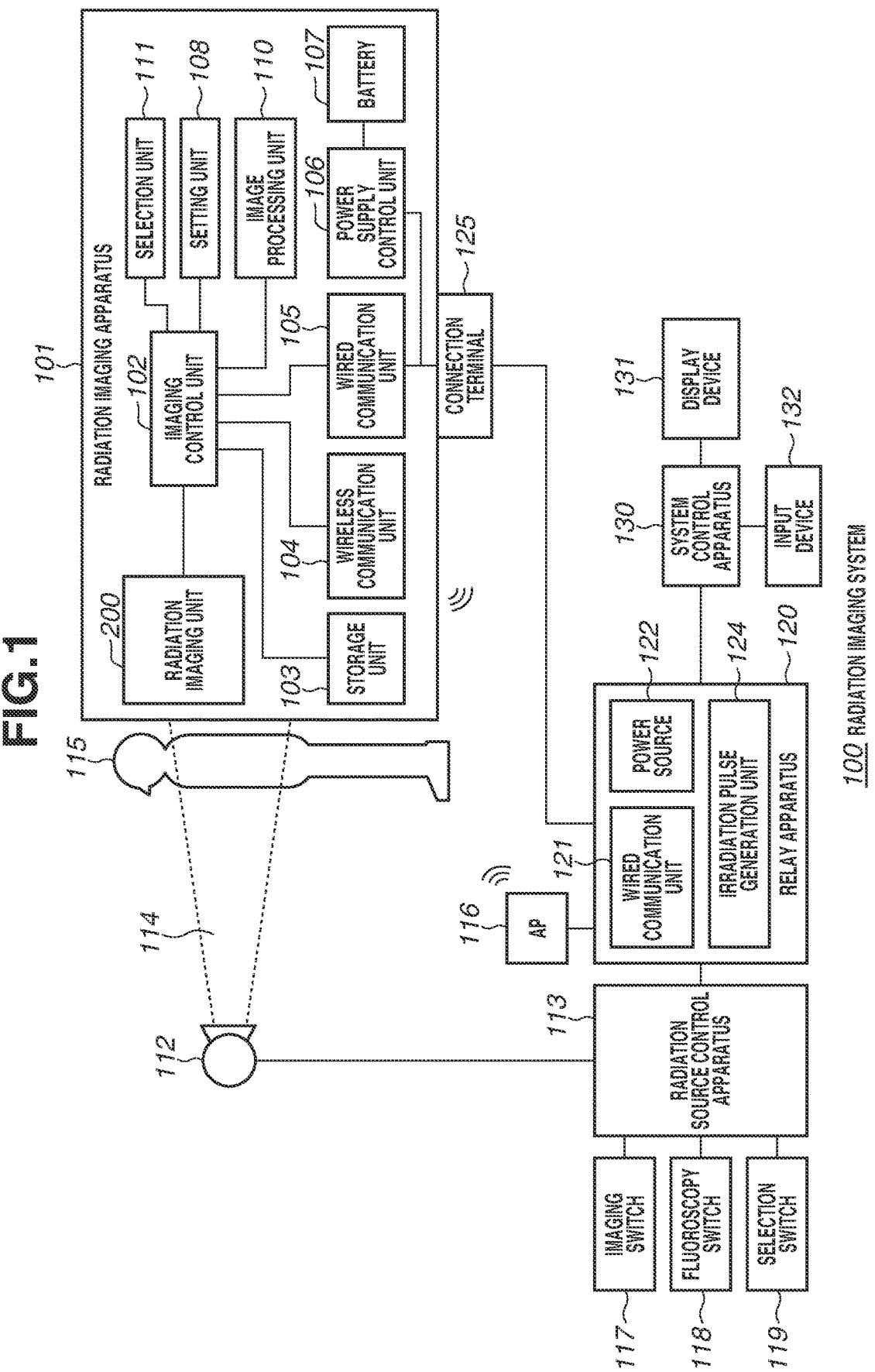
FIG. 1 is a diagram illustrating a schematic configuration example of a radiation imaging system according to a first exemplary embodiment.

FIG. 1 is a diagram illustrating a schematic configuration example of a radiation imaging system 100 according to a first exemplary embodiment of the disclosure. The radiation imaging system 100 includes a radiation imaging apparatus 101, a radiation source 112, a radiation source control apparatus 113, a wireless access point (AP) 116, a relay apparatus 120, and a system control apparatus 130, as illustrated in FIG. 1. The AP 116 can be integral with the relay apparatus 120, or can be excluded without using wireless communication. Further, although not illustrated, the radiation imaging system 100 can be connected to a radiology information system (RIS), a picture achieving and communication system (PACS), a printer, and other devices. In the following description, the term "unit" may refer to a circuit, a device, a hardware component, or a functionality, a functional module, a function, a subprogram, or similar components that are implemented by a processor executing a program stored in a memory device.

The radiation imaging apparatus 101 can communicate with the relay apparatus 120 as an external apparatus. Specifically, the radiation imaging apparatus 101 can communicate over a wired path with the relay apparatus 120 as an external apparatus. The radiation imaging apparatus 101 includes a housing provided with an external connection terminal (not illustrated) connecting to a connection terminal 125 of a wire cable. Further, the radiation imaging apparatus 101 can wirelessly communicate with the relay apparatus 120 as an external apparatus via the AP 116. The radiation imaging apparatus 101 includes a radiation imaging unit 200, an imaging control unit 102, a storage unit 103, a wireless communication unit 104, a wired communication unit 105, a power supply control unit 106, a battery 107, a setting unit 108, an image processing unit 110, and a selection unit 111, as illustrated in FIG. 1. The wireless communication unit 104 may be excluded with wired communication alone, and the battery 107 may be excluded with power supplied from the outside.

The radiation imaging unit 200 detects radiation 114 (including radiation passing through an object 115) emitted from the radiation source 112, and acquires image data to be a radiation image of the object 115. In this process, the radiation imaging unit 200 can acquire image data of a still image and a moving image as the image data. Further, it is suitable to use a flat panel detector as the radiation imaging unit 200, for example.

The imaging control unit 102 performs various controls related to radiation imaging performed by the radiation imaging apparatus 101. The imaging control unit 102 controls driving of the radiation imaging unit 200, imaging in acquiring radiation image data from the radiation imaging unit 200, storage of the acquired image data, and transfer of the acquired image data to an external apparatus. Further, the imaging control unit 102 controls storage of image data in the storage unit 103, transfer of image data to the relay apparatus 120 via the wireless communication unit 104 and the wired communication unit 105. Furthermore, the imaging control unit 102 controls setting of driving timing and driving conditions for the radiation imaging unit 200. In other words, the imaging control unit 102 can control imaging performed by the radiation imaging unit 200 by controlling driving of the radiation imaging unit 200 based on the various setting values.

The relay apparatus 120 and/or the system control apparatus 130 to be described below can include some or all of the functions of the image processing unit 110 of the radiation imaging apparatus 101, depending on the system configuration.

The storage unit 103 stores programs for controlling operation of the radiation imaging apparatus 101, and various kinds of information and various data for such control. Further, the storage unit 103 stores various kinds of information and various data such as that obtained by processing performed by the imaging control unit 102. For example, the storage unit 103 stores image data obtained by the imaging control unit 102 and image data after correction, based on the control by the imaging control unit 102.

The wireless communication unit 104 performs wireless communication with the relay apparatus 120 via the AP 116 in, for example, a wireless local area network (LAN). The wired communication unit 105 performs wired communication with the relay apparatus 120 through wiring (cables). The imaging control unit 102 performs such communications as command communication, radiation synchronization control communication, and image data communication with the relay apparatus 120, using either one or both the wireless communication unit 104 or/and the wired communication unit 105. For example, wired communication with Ethernet® can be performed as wired communication between the radiation imaging apparatus 101 and the relay apparatus 120. Instead of wireless communication between the radiation imaging apparatus 101 and the relay apparatus 120 via the AP 116 is illustrated in FIG. 1, direct wireless communication between them may be performed with the radiation imaging apparatus 101 or the relay apparatus 120 serving as an access point. Further, a communication technique such as wireless fidelity (Wi-Fi) or Bluetooth® can be used in wireless communication. Wireless communication between the radiation imaging apparatus 101 and the system control apparatus 130 is established with them set beforehand as connection destinations to each other.

The power supply control unit 106 controls a power source for supplying power to each of the components of the radiation imaging apparatus 101, such as the radiation imaging unit 200 and the imaging control unit 102, based on the control by the imaging control unit 102.

The battery 107 is a power source in the radiation imaging apparatus 101. In wired communication, for example, the power supply control unit 106 supplies power to each of the components of the radiation imaging apparatus 101 using a power source 122 of the relay apparatus 120 as an external apparatus to cause each of these components to operate. With wired communication disconnected, the power supply control unit 106 supplies power to each of the components of the radiation imaging apparatus 101 using the battery 107 in the radiation imaging apparatus 101 to cause each of these components to operate. In the present exemplary embodiment, the battery 107 is disposed in the radiation imaging apparatus 101, but may be configured as a battery detachable from the radiation imaging apparatus 101. Further, the battery 107 of the present exemplary embodiment is a device that can be charged by power supplied from the outside. A secondary battery such as a lithium ion battery or a nickel metal hydride battery, or an electric storage device such as a lithium ion capacitor or an electric double layer capacitor can also be used for the battery 107.

The radiation source 112 is a device to generate the radiation 114 such as X-rays. The radiation source 112 includes an electron gun and a rotor. In this case, electrons accelerated by a high voltage generated by the radiation source control apparatus 113 collide with the rotor to generate the radiation 114.

The system control apparatus 130 is an apparatus to generally control operation of the radiation imaging system 100. The system control apparatus 130 performs various controls such as operation of the radiation imaging system 100, and acquisition, input, and setting of imaging protocols, and data processing on radiation images captured by the radiation imaging apparatus 101. The system control apparatus 130 has the application functionality of operating on a computer. In other words, the system control apparatus 130 includes at least one processor and at least one memory, and the processor runs programs stored in the memory to work each of function units that will be described below. Alternatively, some or all of the function units may be worked by dedicated hardware. For example, any of various computers and workstations can be suitably used for the system control apparatus 130. The system control apparatus 130 is connected to a display device 131, such as a display, to display menu information about controls and radiation images after imaging, and an input device 132, such as a mouse and a keyboard, to perform various inputs. The system control apparatus 130 outputs images to the display device 131 and provides a graphical user interface using the display device 131, while controlling the operation of the radiation imaging apparatus 101. The above example is in which the system control apparatus 130, the display device 131, and the input device 132 are separate from one another, but a portable information terminal such as a laptop personal computer (PC) or a tablet may be used.

The relay apparatus 120 functions as an interface apparatus connected to the radiation imaging apparatus 101, the system control apparatus 130, and the radiation source control apparatus 113. The relay apparatus 120 is connected to the system control apparatus 130 with Ethernet® or the like, and also functions as a relay apparatus in transferring image data acquired by the radiation imaging apparatus 101 to the system control apparatus 130. The relay apparatus 120 includes a wired communication unit 121 to perform wired communication with the radiation imaging apparatus 101, the power source 122 to supply power to the radiation imaging apparatus 101, and an irradiation pulse generation unit 124 to issue an irradiation request to the radiation source control apparatus 113. The relay apparatus 120 performs synchronous communication with the radiation imaging apparatus 101 and the radiation source control apparatus 113 to perform notification of information about an imaging request switch and perform control to synchronize the image acquisition timing and the radiation irradiation timing of the radiation source control apparatus 113.

The radiation source control apparatus 113 controls the radiation 114 generated from the radiation source 112. The radiation source control apparatus 113, for example, is connected to switches for requesting radiation irradiation, such as an imaging switch 117 and a fluoroscopy switch 118, and, in some cases, to an operation unit for setting irradiation conditions for radiation. For example, in performing imaging for recording or diagnosis, such as still-image capturing for capturing a radiation image in one frame, pressing the imaging switch 117 starts irradiation with radiation under irradiation conditions based on settings corresponding to the imaging switch 117. Here, the imaging switch 117 corresponds to a third switch in some embodiments of the disclosure. In addition, pressing the fluoroscopy switch 118 starts irradiation with radiation under irradiation conditions based on settings corresponding to the fluoroscopy switch 118. Further, the radiation source control apparatus 113 can switch between pulse fluoroscopy and continuous fluoroscopy. Here, the pulse fluoroscopy is moving-image capturing for capturing a radiation image in a plurality of frames through repetition of discretely pulsed irradiation in synchronization with the radiation imaging apparatus 101. The continuous fluoroscopy is moving-image capturing for capturing a radiation image in a plurality of frames through continuous emission of a fixed amount of radiation.

In this case, the radiation source control apparatus 113 includes a selection switch 119 for selecting either the pulse fluoroscopy or the continuous fluoroscopy in response to a press of the fluoroscopy switch 118. The functionality of the fluoroscopy switch 118 and the selection switch 119 corresponds to that of a first switch and a second switch in some embodiments of the disclosure. The imaging switch 117, the fluoroscopy switch 118, and the selection switch 119 each may not be a dedicated switch, and may be buttons on a user interface provided on the radiation source control apparatus 113 by way of example. The radiation source control apparatus 113 to perform continuous fluoroscopy or pulse fluoroscopy may not include the selection switch 119. Further, the imaging switch 117 may be a switch that is operated in two phases: a preparation switch for pre-notifying the radiation imaging apparatus 101 and the radiation source control apparatus 113 of preparation for imaging, and a request switch for requesting actual imaging.

Next, an internal configuration of the radiation imaging unit 200 illustrated in FIG. 1 will be described with reference to FIG. 2. FIG. 2 is a diagram illustrating an internal configuration example of the radiation imaging unit 200 illustrated in FIG. 1. The radiation imaging unit 200 includes a drive circuit 201, a sensor array 202, an amplification circuit 203*a*, a sample-and-hold circuit 203*b*, a multiplexer 201, an amplifier 205, and an analog-to-digital (A/D) converter 206, as illustrated in FIG. 2. Here, the amplification circuit 203*a*, the sample-and-hold circuit 203*b*, the multiplexer 204, the amplifier 205, and the A/D converter 206 are included in a readout circuit 213. That configuration allows the radiation imaging unit 200 to perform imaging of a radiation image in one frame by performing driving of a plurality of pixels 207 to use signals stored in the plurality of pixels 207 based on radiation irradiating the plurality of pixels 207 arranged in a matrix.

The drive circuit 201 drives the plurality of pixels 207 in the sensor array 202, based on the control by the imaging control unit 102.

The sensor array 202 includes the plurality of pixels 207 arranged in a matrix.

Specifically, the plurality of pixels 207 is two-dimensionally arranged in rows and columns in the sensor array 202. Each of the pixels 207 includes a conversion element 209 to convert the incident radiation 114 into signal charge (an electric signal), and a switch element 208 such as a thin-film transistor (TFT) to transfer the electric signal to the outside. In the present exemplary embodiment, the conversion element 209 includes a scintillator (a fluorescence substance) to convert the incident radiation 111 into light such as visible light, and a photoelectric conversion element to convert the converted light into signal charge. The present exemplary embodiment is not limited to this configuration, and a conversion element of so-called direct conversion type with no scintillator to directly convert the incident radiation 114 into a signal can also be used as the conversion element 209.

The drive circuit 201 switches the switch element 208 between ON and OFF via a drive line 211 to perform charge storage and charge readout of the conversion element 209, providing a resultant radiation image. Specifically, the drive circuit 201 applies an ON voltage of the switch element 208 to a predetermined drive line 211 to switch ON the switch element 208 of each of the pixels 207 in the row connected to the predetermined drive line 211. Subsequently, the charge of the conversion element 209 is amplified in the amplification circuit 203a via the corresponding one of the signal lines 210, and held in the sample-and-hold circuit 203b. Afterward, the signals held in the sample-and-hold circuit 203b are sequentially read out via the multiplexer 204, and then amplified by the amplifier 205, and then converted into digital radiation image data by the A/D converter 206. Further, the drive circuit 201 applies an OFF voltage of the switch element 208 to a predetermined drive line 211 to return each of the pixels 207 in the row in which the readout of the charge is completed to the charge storage state. The drive circuit 201 sequentially drives and scans the pixels 207 in each row of the sensor array 202, and the signal charge of each of the pixels 207 is eventually converted into a digital value. That enables read out of the image data. Such driving and readout operations of the radiation imaging unit 200 are controlled by the imaging control unit 102 illustrated in FIG. 1.

Further, the imaging control unit 102 sets the current operation state of the radiation imaging unit 200 based on information about the setting unit 108 holding an imaging order and imaging mode information specified by the system control apparatus 130, and controls the driving of the radiation imaging unit 200. Furthermore, in response of a receipt of an imaging request signal from the relay apparatus 120, the imaging control unit 102 can perform imaging operation for a moving image for fluoroscopy or for a still image in synchronization with the relay apparatus 120. Subsequently, the imaging control unit 102 performs image processing on image data acquired through the imaging operation, and then stores the image data in the storage unit 103 or transfers the image data to an external apparatus. Specifically, the image data is transferred from the radiation imaging apparatus 101 via the relay apparatus 120 to the system control apparatus 130.

The pixels 207 in the sensor array 202 each have different characteristics from one another. Examples of main characteristic variations are variations in offset (dark current) and gain (conversion efficiency). To deal with those, the image data is subjected to offset correction, gain correction, and further, defective pixel correction, and these corrections in image processing are performed in either the radiation imaging apparatus 101 or an external apparatus such as the relay apparatus 120 or the system control apparatus 130.

Here, FIGS. 3A and 3B each illustrate a setting example of the setting unit 108 to hold an imaging mode and setting values (parameters) thereof specified by the system control apparatus 130 in the radiation imaging apparatus 101.

The example in each of FIGS. 3A and 3B include the imaging switch 117 and the fluoroscopy switch 118, and further, either the pulse fluoroscopy or the continuous fluoroscopy can be set for the fluoroscopy switch 118. The setting unit 108 can assign an imaging mode to each of three target switches, the fluoroscopy switch for the continuous fluoroscopy, the fluoroscopy switch for the pulse fluoroscopy, and the imaging switch. In the setting example in FIG. 3A, an imaging mode A is set for the fluoroscopy switch for the continuous fluoroscopy. The imaging mode A includes imaging parameters to be used for imaging: a frame rate of 30 fps, 2×2 pixel addition, a readout image region of 12 inches, and a gain setting 1. Here, the frame rate is the reciprocal of frame time to read out signals of a radiation image in one frame from the plurality of pixels 207. The pixel addition is to add the signals of the pixels 207 in a plurality of rows through simultaneous driving of the pixels 207 in the rows among the plurality of pixels 207, and read out the added signals using the readout circuit 213. A pixel addition number is the number of the added pixels, and 2×2 corresponds to the pixel addition number in this example. The readout image region is a region of the pixels 207 from which signals are read out by the readout circuit 213 through driving of the pixels 207 and that are some of the plurality of pixels 207. The gain setting is a set amplification factor of the amplification circuit 203a, and expressed here by a numerical value at one of levels into which the amplification factors are classified. Further, an imaging mode B is set for the fluoroscopy switch for the pulse fluoroscopy. The imaging mode B includes imaging parameters to be used for imaging: a frame rate of 15 fps, 2×2 pixel addition, a readout image region of 17 inches, and a gain setting 2. Furthermore, an imaging mode C is set for the imaging switch. The imaging mode C includes imaging parameters to be used for imaging: a frame rate of 4 fps, 1×1 pixel addition, a readout image region of 17 inches, and a gain setting 3. The imaging modes A to C each can be a first mode or a second mode in some embodiments of the disclosure, and imaging performed in each of these modes can be first imaging or second imaging in some embodiments of the disclosure.

Based on these settings, the imaging control unit 102 performs driving control in the imaging operation of the imaging mode A in response to a receipt of an imaging request for the continuous fluoroscopy from the radiation source control apparatus 113, and performs driving control in the imaging operation of the imaging mode B in response to a receipt of an imaging request for the pulse fluoroscopy. Further, in response to a receipt of an imaging request for the imaging switch, the imaging control unit 102 performs driving control in the imaging operation of the imaging mode C.

For example, the settings illustrated in FIG. 3B are used to perform imaging of a single still-image with the imaging switch 117 like still-image capturing (general imaging)

without performing imaging with the fluoroscopy switch. In this case, the fluoroscopy switches for the continuous fluoroscopy and the pulse fluoroscopy are assigned settings indicating an invalid (not to be used) switch, and a still image mode D with imaging parameters that are a single frame, 1×1 pixel addition, a readout image region of 17 inches, and a gain setting 3 is set for the imaging switch. Here, for example, the frame time of this imaging may be applied to the single capturing parameter.

Next, a procedure example of imaging operation in the entire radiation imaging system 100 will be described with reference to FIG. 4. First, upon the system activation, information indicating that the fluoroscopy mode is selected is notified to the radiation imaging apparatus 101 via the relay apparatus 120 based on the state of the fluoroscopy switch 118 of the radiation source control apparatus 113, before imaging is performed (at timing TC401). A user selects an imaging protocol, using the input device 132 of the system control apparatus 130 (at timing TC402). Based on the selected imaging protocol, designated commands are notified from the system control apparatus 130 via the relay apparatus 120 to the radiation imaging apparatus 101 (at timing TC403), and set in the setting unit 108. Here, the designated commands include the imaging mode A to be set for the continuous fluoroscopy, the imaging mode B to be set for the pulse fluoroscopy, and the imaging mode C to be set for the still-image capturing. Here, due to the pulse-fluoroscopy selected state at the timing TC401, the imaging control unit 102 may switch the standby mode to the imaging mode B set for the pulse fluoroscopy.

Subsequently, the imaging switch 117 is pressed and then the imaging operation of the imaging mode C is performed (at timing TC404). Control 500 at the time of starting the imaging will be described with reference to FIG. 5.

FIG. 5 is a timing chart illustrating a driving switching control example in starting imaging in the radiation imaging apparatus 101. For example, at timing TC501, the standby driving is controlled with the parameters of the imaging mode B, as the standby driving for no imaging. Here, control of repeating storage and readout is performed at the frame rate or in the frame time defined in the imaging mode B. As this control is performed in the standby period for no imaging, image data read out from the radiation imaging unit 200 is not transferred to an external apparatus such as the system control apparatus 130. Next, the preparation switch is pressed at timing TC502, and the request switch is pressed at timing TC503. Here, the imaging mode C is set for the imaging switch in the setting unit 108. The imaging mode in the current standby operation and the set imaging mode are different, and the imaging control unit 102 starts switching control at timing TC504. Here, the switching control has been described to start at the timing TC504, but may start at the timing TC503. In the switching control, readout driving is performed a plurality of times to solve instability of charge generated in the radiation imaging unit 200 immediately after switching to an imaging mode with different imaging parameters. At the timing TC504, for example, immediately after the start of switching, the readout driving for the imaging mode C after the switching is performed a plurality of times sequentially, releasing charge in the pixels. Subsequently, the readout driving is performed once at the same frame rate and with the same imaging parameters as those of the imaging mode C, as a preparation for the imaging operation in the imaging mode C. This completes the mode switching control, and at timing TC505 for the next storage, the control is performed of emitting the radiation (timing TC506), and the imaging operation based on the imaging mode C after the switching begins. Upon start of the imaging operation, image data acquired based on the readout control is transferred to an external apparatus (at timing TC507).

Here, the switching control is not limited to the example described above.

For example, it is conceivable to use a method of performing the readout driving a fixed number of times at the same frame rate and with the same imaging parameters as those of the imaging mode after the switching. It is also conceivable to use a method of performing the readout driving for the imaging mode after the switching a fixed number of times at a cycle higher than the frame rate of the imaging mode after the switching.

With the standby mode for no imaging different from the set imaging mode, the switching control is performed with a mode switching time T_mc between the press of the switch and the actual imaging operation. This mode switching time is uniquely defined based on the imaging mode after the switching.

Referring back to FIG. 4, the imaging switch 117 is released at timing TC405, and the imaging in the imaging mode C ends. In response to the end of the imaging (the first imaging) in the imaging mode C, the selection unit 111 selects a setting value for the standby driving by selecting a standby mode from the setting information about the setting unit 108. In this case, the setting value for the standby driving is set to the setting value for the imaging mode B, by selecting the imaging (the second imaging) in the imaging mode B set for the pulse fluoroscopy. In response to this setting, the standby operation is performed with the setting value for the imaging mode B, so that the mode switching control is performed. After the mode switching time T_mc, the mode switching is completed, and the standby state begins with the standby driving set based on the setting value for the imaging mode B (at timing TC406). Here, the setting value for the standby driving may not be set to the setting value for the standby driving with the second setting value as the setting value for the second imaging, and a second setting value as the setting value for the standby driving closer than the first setting value as the setting value for the first imaging can reduce or decrease an artifact after the switching. The standby operation is to drive the plurality of pixels 207 to reduce or decrease the signals (or the amount of dark current components) stored in the plurality of pixels 207 during the period in which the plurality of pixels 207 is not irradiated with the radiation. The end of the imaging can be performed in response to the end of the press of the switch, or may be performed in response to the end of the driving for the plurality of pixels in the imaging or the end of the readout therefrom. Moreover, not all the setting values may be used, and if the operation is performed for at least one setting value, an effect of this setting value is produced.

Subsequently, when the fluoroscopy switch 118 is pressed with the pulse fluoroscopy mode selected (at timing TC407), the parameters set for the pulse fluoroscopy and the parameters for the current standby operation match each other. This allows the fluoroscopic imaging in the imaging mode B to start without performing the switching control separately during the standby period. Control 600 at the start of the fluoroscopic imaging will be described with reference to FIG. 6.

Figure 6:
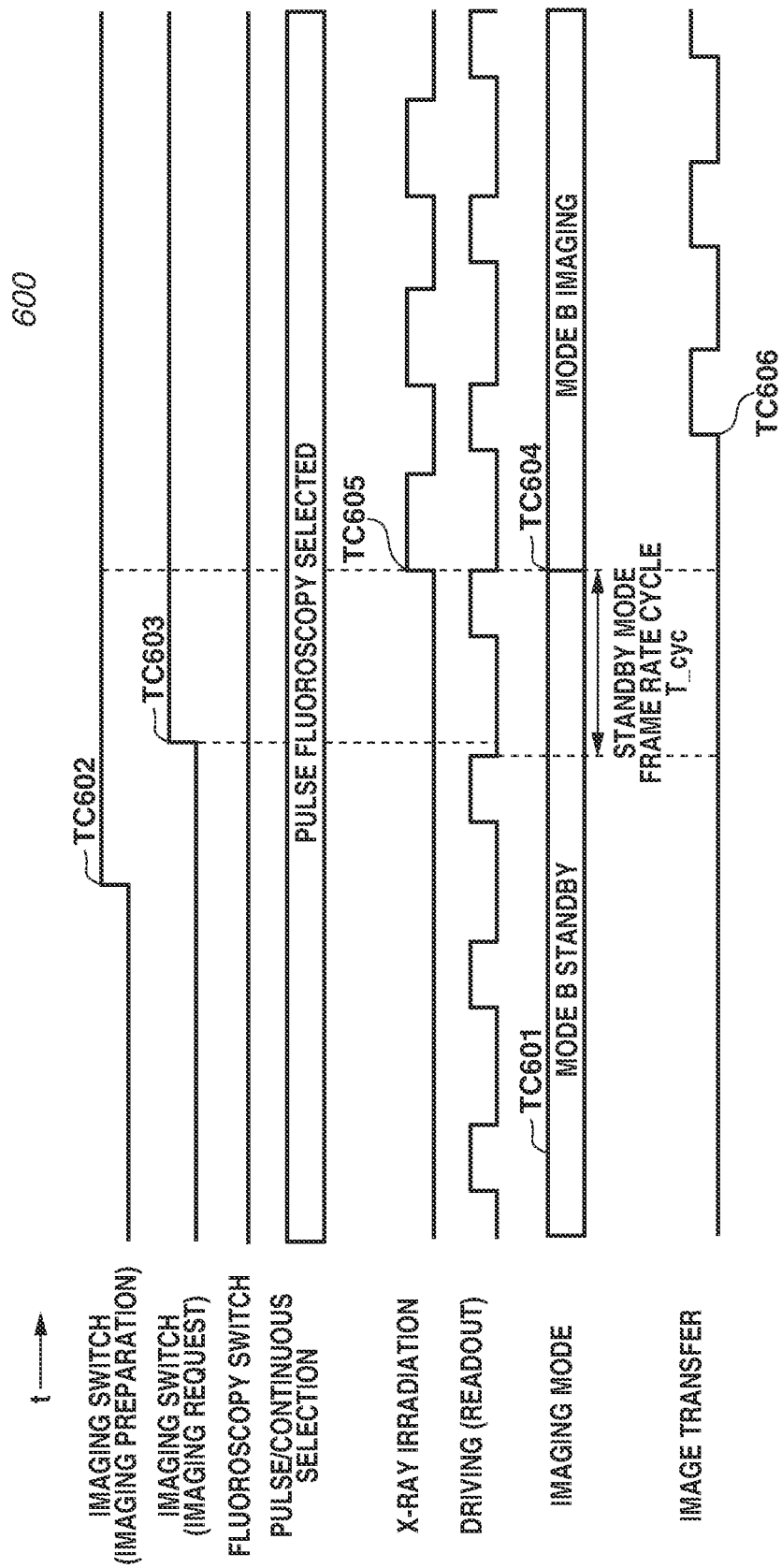
FIG. 6 is a timing chart illustrating an imaging operation example of the radiation imaging system according to the first exemplary embodiment.

If the imaging parameters for the standby operation for no imaging and the imaging parameters for the set imaging mode match each other as illustrated by an example in FIG. 6, the switching control will not be performed separately.

Thus, after the timing of the press of the imaging request switch (at timing TC603), control of the irradiation of the radiation at timing TC605 and start of the imaging operation are possible at the next storage start timing TC604. In this case, a variation in the time by a frame rate cycle T_cyc however occurs after the timing of the press of the switch and before the imaging operation actually begins, causing a delay of a T_cyc time at maximum to occur. In standby in an imaging mode at a high frame rate, the T_cyc time is short and thus does not matter, but in standby in an imaging mode at a low frame rate, the frame rate cycle T_cyc can be longer than the mode switching time T_mc. A frame rate in a fluoroscopy mode is typically higher than in an imaging mode for imaging a still image, and it thus is suitable that a setting value for the fluoroscopy mode is selected as a setting value for the standby driving.

Figure 7:
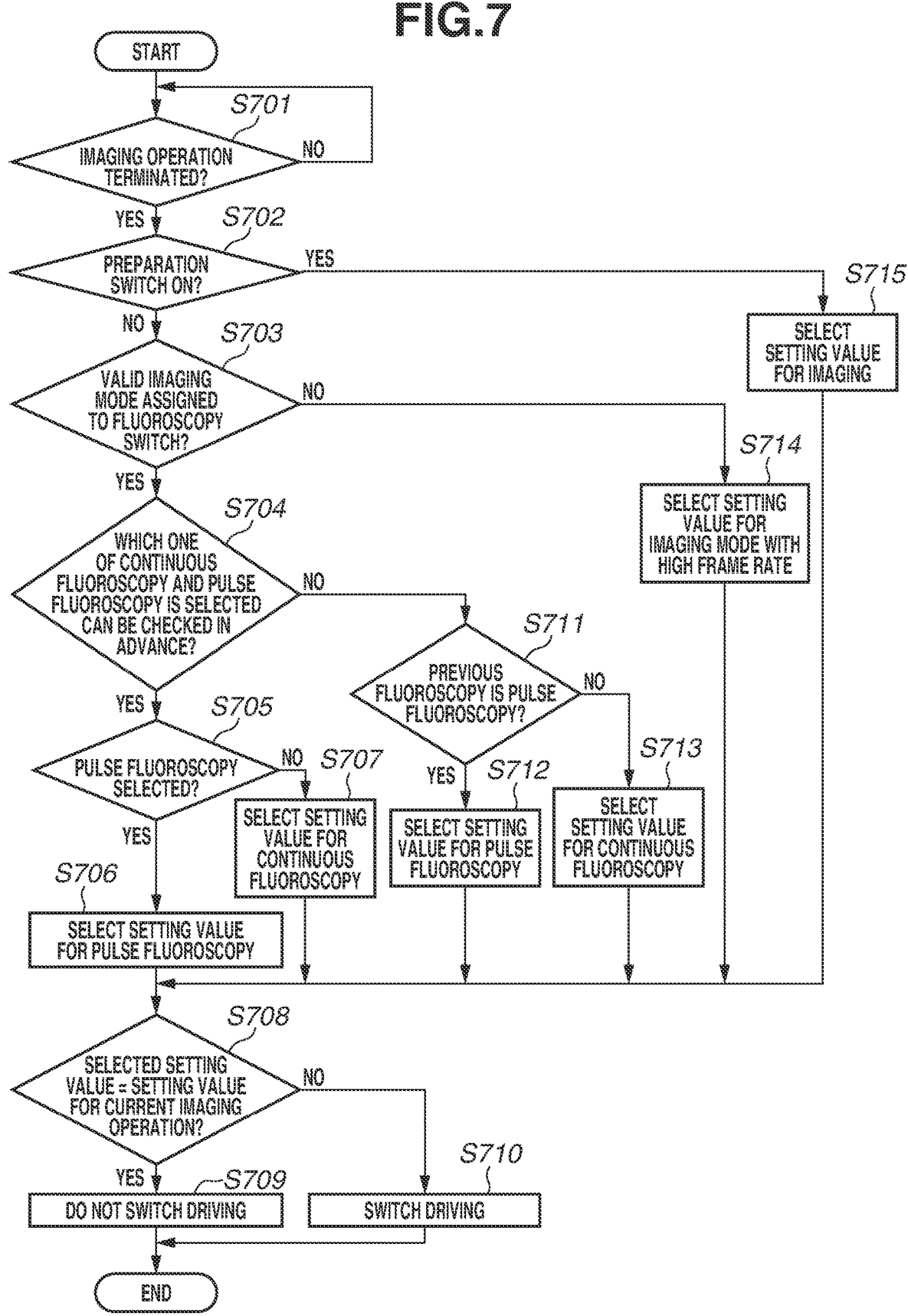
FIG. 7 is a flowchart illustrating a selection processing example according to the first exemplary embodiment.

FIG. 7 is a flowchart illustrating a processing example in the selection unit 111 of the radiation imaging apparatus 101 according to the first exemplary embodiment.

In step S701, the selection unit 111 determines whether the imaging operation such as the fluoroscopic imaging, the still-image capturing, or the continuous imaging is terminated. If the imaging operation is terminated (YES in step S701), the processing proceeds to step S702 to start determination as to the selection for the standby driving. In step S702, with the imaging switch 117 composed of the preparation switch and the request switch as a two-phase switch, the state of each of these switches being to be notified from the radiation source control apparatus 113 to the radiation imaging apparatus 101, the selection unit 111 checks whether the preparation switch is still in a pressed state after the imaging operation is terminated. If the preparation switch alone is pressed (YES in step S702), the imaging operation by the imaging switch 117 is likely to be performed next. For that reason, the processing proceeds to step S715, and in step S715, the selection unit 111 selects a setting value for an imaging mode set for the imaging switch 117 in the setting unit 108, as a setting value for the standby driving. Despite the description as in step S715 in the processing example, a low frame rate of the imaging mode set for the imaging switch 117 may cause the frame rate cycle T_cyc to be longer than the mode switching time T_mc or switching to that imaging mode. In this case, the processing may proceed to step S703 in which the selection unit 111 selects a setting value for the standby driving, other than the setting value for the imaging mode set for the imaging switch 117.

If the preparation switch is not pressed (NO in step S702), the processing proceeds to step S703. In step S703, the selection unit 111 checks whether a valid imaging mode is set for the fluoroscopy switch 118 of either the continuous fluoroscopy or the pulse fluoroscopy. If the setting of invalid (not to be used) is made for both of these switches (NO in step S703), the processing proceeds to step S714. In step S714, the selection unit 111 selects a setting value for an imaging mode with a high frame rate as a setting value for the standby driving from the imaging modes that can be performed by the imaging control unit 102.

If a valid imaging mode is assigned to the fluoroscopy switch 118 (YES in step S703), the processing proceeds to step S704. In step S704, the selection unit 111 determines whether which of the continuous fluoroscopy mode and the pulse fluoroscopy mode is selected in the radiation source control apparatus 113 can be checked in advance. This information is notified via the relay apparatus 120 to the radiation imaging apparatus 101, in response to, for example, a switching operation on the selection switch 119.

However, a system of notifying the fluoroscopy mode selection information at the moment of a press of the fluoroscopy switch alone as an example will have difficulty checking in advance. In this case (NO in step S704), the processing proceeds to step S711, and in step S711, the selection unit 111 determines whether the previously performed fluoroscopy is the pulse fluoroscopy. If the previously performed fluoroscopy is the pulse fluoroscopy (YES in step S711), the processing proceeds to step S712, and in step S712, the selection unit 111 selects a setting value for the pulse fluoroscopy as a setting value for the standby driving. Otherwise (NO in step S711), the processing proceeds to step S713, and in step S713, the selection unit 111 selects a setting value for the continuous fluoroscopy as a setting value for the standby driving.

If which one of the continuous fluoroscopy mode and the pulse fluoroscopy mode is selected can be checked in advance (YES in step S704), the processing proceeds to step S705. In step S705, the selection unit 111 determines whether the pulse fluoroscopy is selected. If the pulse fluoroscopy is selected (YES in step S705), the processing proceeds to step S706, and in step S706, the selection unit 111 selects a setting value for the pulse fluoroscopy as a setting value for the standby driving. If the continuous fluoroscopy is selected (NO in step S705), the processing proceeds to step S707, and in step S707, the selection unit 111 selects a setting value for the continuous fluoroscopy as a setting value for the standby driving.

In step S708, whether the setting value for the standby driving thus selected by the selection unit 111 is the same as the setting value for the imaging mode in the current imaging operation is determined. If the selected setting value is different from the setting value for the imaging mode in the current imaging operation (NO in step S708), the processing proceeds to step S710, and in step S710, switching control is immediately performed based on the setting value for the standby driving. If the selected setting value is the same as the setting value for the imaging mode in the current imaging operation (YES in step S708), the processing proceeds to step S709, and in step S709, switching for driving is not performed.

As described above, performing the standby driving suitable for the next fluoroscopy reduces the delay from the press of the fluoroscopy switch to the start of the fluoroscopic imaging operation on the radiation imaging apparatus used as the fluoroscopic apparatus. The pulse fluoroscopy, the still-image capturing, and the continuous fluoroscopy each have been described above as an imaging operation, but, for example, operation of acquiring an image without emitting the radiation and acquiring offset correction data for correcting the offset component may also be included as one imaging operation.

Figure 8:
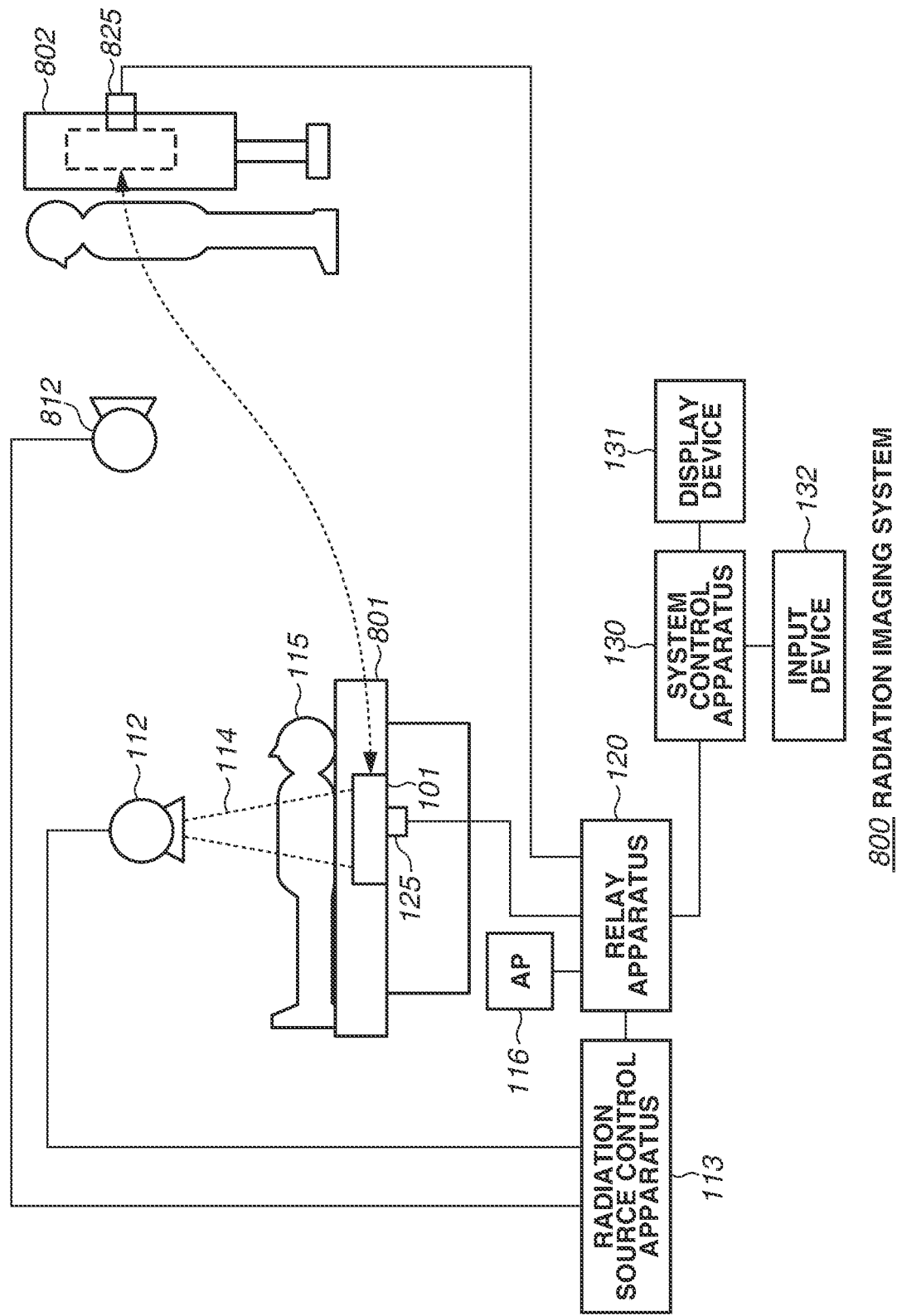
FIG. 8 is a diagram illustrating a schematic configuration example of a radiation imaging system according to a second exemplary embodiment

Next, a second exemplary embodiment will be described with reference to FIGS. 8 and FIG. 9. As illustrated in FIG. 8, a radiation imaging system 800 in the second exemplary embodiment includes a plurality of radiation sources, i.e., a radiation source 112 and a radiation source 812 used for, for example, a fluoroscopic table 801 and an upright support 802, respectively. A radiation imaging apparatus 101 used in the fluoroscopic table 801 is connected to a connection terminal 125 of a wire cable for use to perform imaging operation such as pulse fluoroscopy, continuous fluoroscopy, and still-image capturing. A cooling device (not illustrated) such as an air-cooling device is separately held in the fluoroscopic table 801 to stabilize the temperature of the radiation imaging apparatus 101.

Here, the radiation imaging apparatus 101 can be easily taken out of the fluoroscopic table 801, and can be disconnected from the connection terminal 125 of the wire cable and moved. The radiation imaging apparatus 101 can be then connected to a connection terminal 825 of a wire cable of the upright support 802 to perform the still-image capturing as general imaging in the upright support 802. The radiation imaging apparatus 101 can determine which one of the connection terminals of the wire cables is connected thereto, and thus can determine whether the radiation imaging apparatus 101 is to be used in the fluoroscopic table 801 or the upright support 802. One conceivable method as an example is of holding in a relay apparatus 120 a setting indicating which one of the connection terminal 125 of the wire cable for the fluoroscopic table 801 and the connection terminal 825 of the wire cable for the upright support 802 is to be used, and notifying the setting through command communication with the radiation imaging apparatus 101 connected. Here, although the radiation imaging apparatus 101 used in the upright support 802 is connected to the connection terminal 825 of the wire cable, the radiation imaging apparatus 101 can be used through wireless communication using an AP 116, instead of the wire connection. The radiation imaging apparatus 101 can be used for imaging at any location through wireless communication, in addition to the use in the fluoroscopic table 801 and the upright support 802. In this case, the radiation imaging apparatus 101 operates on a built-in battery. In the present exemplary embodiment, the configurations of the radiation imaging apparatus 101, a radiation source control apparatus 113, the relay apparatus 120, and a system control apparatus 130 are similar to those of the first exemplary embodiment.

In the radiation imaging system 800 described above the radiation imaging apparatus 101 operating on a built-in battery out of the fluoroscopic table 801 will consume the battery more if standby operation is performed. In an imaging mode for fluoroscopic, as in the fluoroscopic table 801, for example. In addition, the radiation imaging apparatus 101 taken out of the fluoroscopic table 801 is also separated from the cooling device, and the configuration involves preventing a temperature rise in the radiation imaging apparatus 101.

Figure 9:
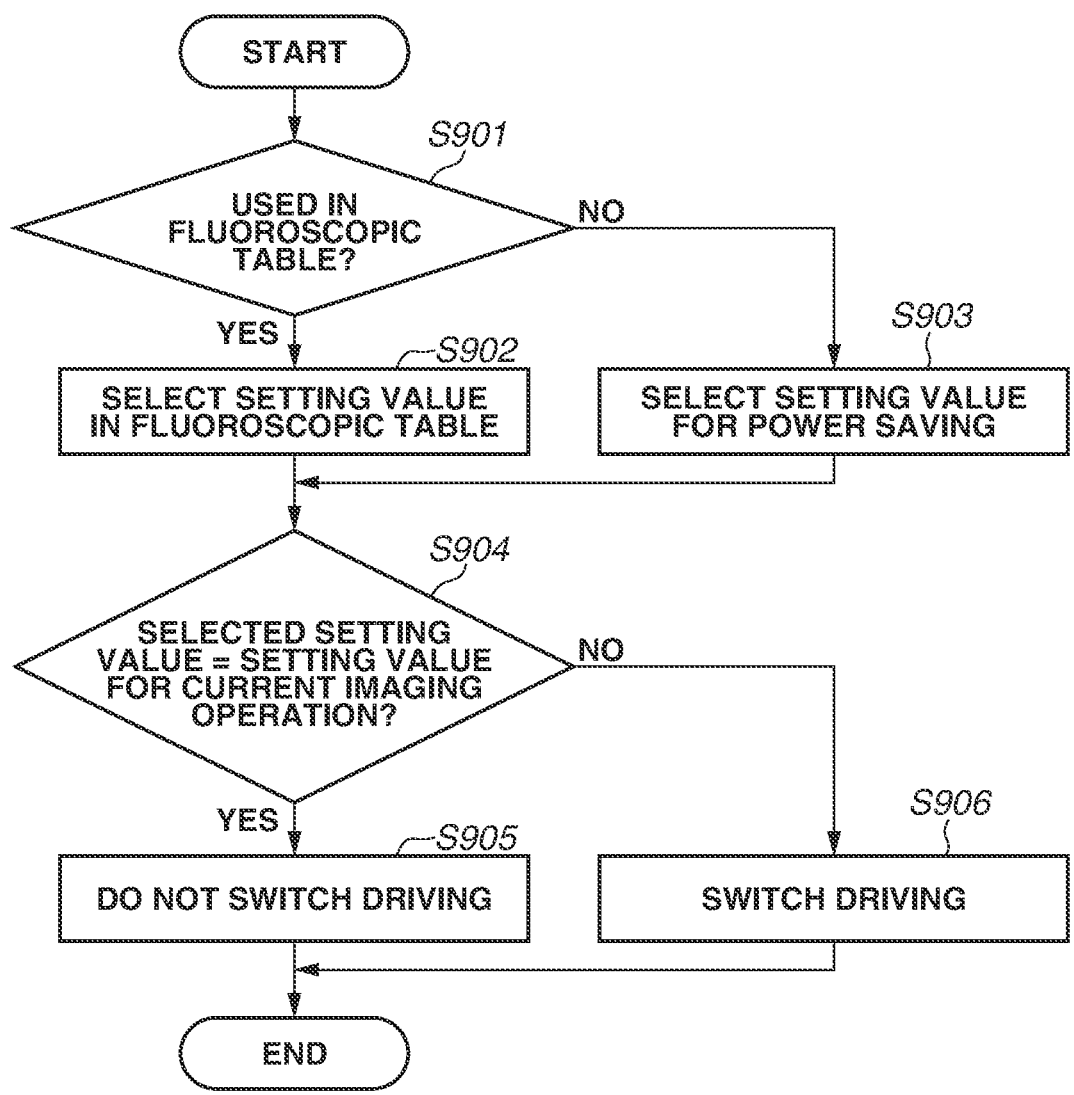
FIG. 9 is a flowchart illustrating a selection processing example according to the second exemplary embodiment.

FIG. 9 is a flowchart illustrating a processing example in a selection unit 111 of the radiation imaging apparatus 101 according to the second exemplary embodiment of the disclosure. In step S901, the selection unit 111 checks whether the radiation imaging apparatus 101 is in use in the fluoroscopic table 801. If the radiation imaging apparatus 101 is out of use in the fluoroscopic table 801 (NO in step S901), the processing proceeds to step S903. In step S903, the selection unit 111 selects to a setting value for the standby driving a setting value for an imaging mode for power saving of reducing power consumption down to a level lower than that in the image operation to prevent a rise in power consumption and temperature of the radiation imaging apparatus 101. If the radiation imaging apparatus 101 is in use in the fluoroscopic table 801 (YES in step S901), the processing proceeds to step S902. In step S902, the selection unit 111 selects a setting value for the standby driving in the fluoroscopic table 801. For the selection processing for the setting value for the standby driving in the fluoroscopic table 801 (step S902), specifically, for example, it is conceivable to use a method similar to the processing of selecting the setting value for the standby driving in the first exemplary embodiment in FIG. 7.

Subsequently, in step S904, whether the selected setting value for the standby driving is the setting value for the current imaging mode in which an imaging control unit 102 is in operation is determined. If the selected setting value for the standby driving is different from the setting value for the current imaging mode (NO in step S904), the processing proceeds to step S906, and in step S906, the setting value is switched to the selected setting value for the standby driving. If the selected setting value for the standby driving is the setting value for the current imaging mode (YES in step S904), the processing proceeds to step S905, and in step S905, the standby driving is performed as it is.

According to the second exemplary embodiment, the setting value for the standby driving can be selected as appropriate based on the use state. For example, in use in the fluoroscopic table 801, a setting value selected beforehand for the standby driving suitable for the next fluoroscopic operation allows the delay from the press of a fluoroscopy switch to the start of the fluoroscopy imaging operation to be reduced. In addition, in use outside the fluoroscopic table 801, a switched setting value for the standby driving for power saving allows reduction of a rise in temperature and power consumption.

(Other Exemplary Embodiments)

The disclosure can also be implemented by processing for loading a program for implementing one or more functions in any of the above-described exemplary embodiments to a system or apparatus via a network or a storage medium and causing one or more processors in a computer of the system or apparatus to read and run the program. The disclosure can also be implemented by a circuit (for example, an application specific integrated circuit (ASIC)) that implements the one or more functions.

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)?), a flash memory device, a memory card, and the like.

According to the exemplary embodiments of the disclosure, a radiation imaging apparatus is provided that can perform imaging in a plurality of imaging modes, and that can control switching to an imaging mode suitable for use as a fluoroscopic apparatus during a standby period.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2020-196897, filed Nov. 27, 2020, which is hereby incorporated by reference herein in its entirety.

What is claim is:

1. A radiation imaging apparatus comprising:
 a radiation imaging unit configured to perform an imaging of a radiation image in one frame by performing a driving of a plurality of pixels to use signals stored in the plurality of pixels based on radiation irradiating the plurality of pixels arranged in a matrix; and
 an imaging control unit configured to control the imaging by controlling the driving of the plurality of pixels based on a setting value,
 wherein the imaging control unit causes the radiation imaging unit to perform the imaging in a plurality of modes varying in the setting value, and
 wherein the imaging control unit causes the radiation imaging unit to perform a standby driving of the plurality of pixels to reduce signals stored in the plurality of pixels during a period in which the plurality of pixels is not irradiated with radiation, the plurality of modes including a first mode in which the radiation imaging unit performs a first imaging using a first setting value and a second mode in which the radiation imaging unit performs a second imaging using a second setting value different from the first setting value after the first imaging, and the imaging control unit causes the radiation imaging unit to perform the standby driving using the setting value closer to the second setting value than to the first setting value in response to an end of the first imaging in causing the radiation imaging unit to perform the second imaging.

2. The radiation imaging apparatus according to claim 1, wherein the radiation imaging unit includes a drive circuit to drive the plurality of pixels, and a readout circuit to amplify signals from the plurality of pixels and read out the amplified signals, and
 wherein the setting value includes at least one of a pixel addition number, a readout time, a frame rate, or a readout image region, the pixel addition number being a number of added pixels from which signals are read out by the readout circuit by simultaneously driving pixels in a plurality of rows of the plurality of pixels to add signals from the pixels in the plurality of rows, the readout time being a time of a readout of signals of a radiation image in one frame from the plurality of pixels by the readout circuit, the frame rate being a reciprocal of the readout time, the readout image region being a region in which pixels of the plurality of pixels are arranged, the pixels from which signals are read out by the readout circuit by the drive circuit being driven.

3. The radiation imaging apparatus according to claim 2, further comprising a setting unit configured to hold the setting value corresponding to each of the plurality of modes,
 wherein the setting unit sets the setting value for the standby driving to the second setting value.

4. The radiation imaging apparatus according to claim 3, further comprising a selection unit configured to select the setting value corresponding to each of the plurality of modes held by the setting unit,
 wherein the setting unit sets the setting value selected by the selection unit to the setting value for the standby driving.

5. A radiation imaging system comprising:
 the radiation imaging apparatus according to claim 1;
 a relay apparatus configured to perform a relay between a radiation source control apparatus to control a radiation source for emitting the radiation and the radiation imaging apparatus; and
 a system control apparatus configured to control an operation of the radiation imaging system generally via the relay apparatus.

6. The radiation imaging system according to claim 5, wherein the plurality of modes includes a pulse fluoroscopy mode in which the radiation imaging apparatus performs an imaging of the radiation image in a plurality of frames based on a plurality of rays of the radiation emitted in a pulse form from the radiation source, and a still image mode in which the radiation imaging apparatus performs an imaging of the radiation image in one frame based on the radiation emitted from the radiation source.

7. The radiation imaging system according to claim 6, wherein the plurality of modes further includes a continuous fluoroscopy mode in which the radiation imaging apparatus performs an imaging of the radiation image in a plurality of frames based on the radiation continuously emitted from the radiation source.

8. The radiation imaging system according to claim 7,
 wherein the radiation source control apparatus controls the radiation source based on an instruction received from a first switch for issuing an instruction to cause the radiation source to emit a plurality of rays of radiation in a pulse form, a second switch for issuing an instruction to cause the radiation source to emit the radiation continuously, and a third switch for issuing an instruction to cause the radiation source to emit the radiation for the still image mode, and
 wherein the radiation imaging apparatus includes a setting unit setting the setting value for the standby driving, based on an instruction from at least one of the first switch, the second switch, or the third switch.

9. The radiation imaging system according to claim 7, wherein the radiation imaging apparatus includes a setting unit setting the setting value for the standby driving, based on an imaging protocol input into the system control apparatus.

10. A method of controlling a radiation imaging apparatus including a radiation imaging unit configured to perform an imaging of a radiation image in one frame by performing a driving of a plurality of pixels to use signals stored in the plurality of pixels based on radiation irradiating the plurality of pixels arranged in a matrix, and controlling the imaging of the radiation image by controlling the driving of the plurality of pixels based on a setting value, the method comprising:
 performing the imaging in a plurality of modes with the radiation imaging unit to perform the imaging in a plurality of modes by varying in the setting value;
 performing a standby driving of the plurality of pixels with the radiation imaging unit to reduce signals stored in the plurality of pixels during a period in which the plurality of pixels is not irradiated with radiation, the plurality of modes including a first mode in which the radiation imaging unit performs a first imaging using a first setting value and a second mode in which the radiation imaging unit performs a second imaging using a second setting value different from the first setting value after the first imaging; and performing a standby driving with the radiation imaging unit using the setting value closer to the second setting value than to the first setting value in response to an end of the first imaging in causing the radiation imaging unit to perform the second imaging.

11. A non-transitory computer readable storage medium storing a program causing a computer to perform the method according to claim 10.

* * * * *